US012263526B2

(12) United States Patent
Foret

(10) Patent No.: US 12,263,526 B2
(45) Date of Patent: Apr. 1, 2025

(54) METHOD FOR THE GENERATIVE PRODUCTION OF A THREE-DIMENSIONAL COMPONENT

(71) Applicant: Messer Industries USA, Inc., Bridgewater, NJ (US)

(72) Inventor: Pierre Foret, Munich (DE)

(73) Assignee: Messer Industries USA, Inc., New Castle, DE (US)

( * ) Notice: Subject to any disclaimer, the term of this patent is extended or adjusted under 35 U.S.C. 154(b) by 0 days.

(21) Appl. No.: 15/726,468

(22) Filed: Oct. 6, 2017

(65) Prior Publication Data

US 2018/0128803 A1    May 10, 2018

(30) Foreign Application Priority Data

Oct. 10, 2016   (DE) ..................... 10 2016 012 116.5

(51) Int. Cl.
| | | |
|---|---|---|
| B22F 10/28 | (2021.01) | |
| B22F 10/32 | (2021.01) | |
| B22F 12/90 | (2021.01) | |
| B23K 26/12 | (2014.01) | |
| B33Y 10/00 | (2015.01) | |

(Continued)

(52) U.S. Cl.
CPC ............ B22F 10/28 (2021.01); B22F 10/32 (2021.01); B22F 12/90 (2021.01); B23K 26/125 (2013.01); B33Y 40/00 (2014.12); G01N 33/0075 (2013.01); *B22F 2201/11* (2013.01); *B22F 2999/00* (2013.01); *B33Y 10/00* (2014.12); *B33Y 30/00* (2014.12); *Y02P 10/25* (2015.11)

(58) Field of Classification Search
CPC ....................................................... B22F 10/28
See application file for complete search history.

(56) References Cited

U.S. PATENT DOCUMENTS

| | | | | |
|---|---|---|---|---|
| 2016/0045981 | A1* | 2/2016 | Zurecki ................ | B33Y 10/00 |
| | | | | 219/76.12 |
| 2016/0067779 | A1 | 3/2016 | Dautova et al. | |

FOREIGN PATENT DOCUMENTS

| | | | | |
|---|---|---|---|---|
| DE | 202016004832 U1 * | 9/2016 | ......... | G01N 33/0065 |
| EP | 1077803 B1 * | 7/2002 | ............ | B22F 3/1055 |

(Continued)

OTHER PUBLICATIONS

Espacenet translation of DE-202016004832-U1 retrieved on Sep. 23, 2019 (Year: 2016).*

(Continued)

*Primary Examiner* — Jophy S. Koshy
*Assistant Examiner* — Joshua S Carpenter
(74) *Attorney, Agent, or Firm* — Joshua L. Cohen

(57) ABSTRACT

A method for the generative production of a three-dimensional component in a processing chamber, wherein providing a metal starting material in the processing chamber and melting the starting material by inputting energy are repeated, and a process gas is provided in the processing chamber. The method includes the hydrogen content of the process gases or of a sample of the process gas is determined; the oxygen content of the process gas or of a sample of the process gas is determined by an oxygen sensor, and/or the dewpoint of the process gases or of a sample of the process gas is determined; and the value determined for the oxygen content and/or the dewpoint is/are corrected with the value for the hydrogen content determined.

8 Claims, 2 Drawing Sheets

(51) Int. Cl.
  *B33Y 30/00*   (2015.01)
  *B33Y 40/00*   (2020.01)
  *G01N 33/00*   (2006.01)

(56)                References Cited

FOREIGN PATENT DOCUMENTS

| EP | 2774703 A1 | * | 9/2014 | ............ B22F 3/1055 |
| EP | 3 075 470 A1 |   | 10/2016 | |
| JP | H06 265518 A |   | 9/1994 | |
| JP | 2005-232472 | * | 9/2005 | .............. B22F 3/035 |

OTHER PUBLICATIONS

Power et al. Electroanalytical Sensor Technology. Ch 7. Intech. (2013) (Year: 2013).*
"Chapter 6: Chemical Sensors." National Research Council. 1995. Expanding the Vision of Sensor Materials. Washington, DC: The National Academies Press. doi: 10.17226/4782 (Year: 1995).*
Espacenet machine translation of EP1077803B1 retrieved on Jun. 2, 2022 (Year: 2002).*
European Search Report and Written Opinion for 17001609.1-1373, Nov. 13, 2017, Authorized Officer: Gilles Forestier, 11 pages.

* cited by examiner

METHOD FOR THE GENERATIVE PRODUCTION OF A THREE-DIMENSIONAL COMPONENT

CROSS REFERENCE TO RELATED APPLICATIONS

This application claims priority from German Patent Application DE 10 2016 012 116.5 filed on Oct. 10, 2016.

BACKGROUND OF THE INVENTION

The present invention relates to a method for the generative production of a three-dimensional component in a processing chamber, wherein the steps of
providing a metal starting material in the processing chamber
melting the starting material by inputting energy, are repeated multiple times, wherein a process gas is provided in the processing chamber, and wherein the oxygen content of the process gas is determined.

The invention further relates to an apparatus for the generative production of a three-dimensional component, comprising a processing chamber with a structuring platform and an application device for depositing the starting materials on the structuring platform, a laser for melting the starting material and a process gas feed device for feeding process gas into the processing chamber.

Generative production methods can be used to produce an enormous variety of three-dimensional components with complex geometry.

For example 3D printing is used to construct three-dimensional workpieces one layer at a time. Construction is carried out under computer control from or more liquid or solid substances according to predefined dimensions and shapes (CAD). During construction, physical or chemical hardening or melting processes take place. Substances typically utilized for 3D printing are plastics, synthetic resins, ceramics and metals.

3D printers are used in industry and research. Applications also exist in the domestic and entertainment sectors and in art.

3D printing is a generative and/or additive production method. The most important techniques in 3D printing are selective laser melting and electron beam melting for metals and selective laser sintering for polymers, ceramic and metals, stereolithography and digital light processing for liquid synthetic resins, and polyjet modelling and fused deposition modelling for plastics and partly synthetic resins.

A further generative method is topical melting and solidification. In this method type, metal powder or metal wire is melted and solidified one layer at a time so that a three-dimensional component can be generated. The energy input, input by means of a laser beam, is locally limited, so the size of the melt pool formed is small. This makes it possible to create very intricate structures.

Corresponding methods are marketed commercially as Laser Engineered Net Shaping (LENS), Direct Metal Deposition (DMD), Laser Additive Manufacturing (LAM), Selective Laser Melting (SLM), Laser Metal Fusion (LFM) or Laser Metal Deposition (LMD).

In the case of local laser sintering of melting, a distinction is made between indirect and direct methods.

Selective Laser Sintering (SLS) is a method for creating spatial structures from a powdery starter material by sintering. Laser sintering is a generative layer construction method: the workpiece is constructed one layer at a time. In this way, the effect of laser beams can be used to produce any three-dimensional geometries, even with undercuts, e.g., workpieces which cannot be produced by conventional mechanical or casting manufacturing processes.

In selective laser sintering (SLS/LMF), a layer of powder material is deposited on a work surface (structuring platform). The loose powder is melted at specific points by a laser beam. In the process, the powder particles are bonded in the layer and with the layer below according depending on the material used. For the purposes of producing metallic components, two basic development directions can be distinguished. Besides the direct solidification of metallic powder materials by laser irradiation (direct metal laser sintering), the production of metal components by a combination of SLS of plastic-coated metal powder followed by thermal treatment (IMLS) became popular quite early.

In direct metal laser sintering (DMLS), metal materials consisting of a single or multiple components are used. In particular, DMLS multicomponent powders consisting of various alloy elements are used. The low-melting component contained in the powder is melted with a laser beam and flows round the high-melting component, which serves as a support structure.

In electron beam melting (EBM), the workflow is substantially the same as that of the laser-based method. Selected sites of a loose metal powder are melted and then solidified in the desired shaped in the powder bed or via a nozzle or wire. The energy required for this is provided by an electron beam. The method usually takes place in a negative pressure chamber flooded with inert gas.

Accordingly, in generative production methods a powder bed, a powder feed or a wire feed is used, wherein these starting materials are melted and then solidified again by the input of energy, for example by means of a laser beam, an electron beam or a plasma/electric arc. Inert or active gases are also used as the process gases in the generative production methods.

The quality of the components manufactured depends on many parameters, particularly the process gas, its composition, purity, flow velocity etc. In this context, an essential factor is the oxygen content of the process gas, as this has a considerable effect on the component quality.

Generative production methods often take place in a processing chamber which is filled with a process gas. Normally, an inert gas is used for this, and the impurities in the gas must be strictly controlled. For example, the oxygen content must not exceed a certain threshold value.

For example, in the prior art the processing chamber is flushed with argon before the start of the actual manufacturing process until the oxygen content is below a specified limit value, such as 0.1%.

The generative manufacturing process does not start until then. During the manufacturing process, the pressure in the processing chamber is controlled, and further argon is added if the pressure falls below a minimum pressure value. A slight argon overpressure is maintained in the processing chamber to prevent ambient air from getting in. In this way, measures are in place that are designed to keep the oxygen content below the specified limit value of 0.1% for example.

With this known method, the oxygen content is not determined, or not determined precisely, and also not controlled. The method thus does not allow of reproducible process conditions.

SUMMARY OF THE INVENTION

The object of the present invention is therefore to provide a generative production method and corresponding apparatus which enable better, and particularly reproducible adjustment and control of the process gas atmosphere in the processing chamber.

This object is solved with a method for the generative production of a three-dimensional component in a processing chamber, wherein the steps of
providing a metal starting material in the processing chamber
melting the starting material by inputting energy, are repeated multiple times, wherein a process gas is provided in the processing chamber, and wherein the oxygen content of the process gas is determined, and which is characterised in that a first oxygen sensor and a second oxygen sensor are provided, and that the oxygen content of the process gas is determined by means of the first oxygen sensor and/or by means of the second oxygen sensor depending on the desired quality of the component that is to be produced.

An apparatus for the generative production of a three-dimensional component according to the invention, comprising a processing chamber with a structuring platform and an application device for depositing the starting materials on the structuring platform, a laser for melting the starting materials, and a process gas feed device for feeding process gas into the processing chamber differs from other apparatuses in that a first oxygen sensor for determining the oxygen content of the process gas and a second oxygen sensor for determining the oxygen content of the process gas are provided, wherein the second oxygen sensor is designed as a chemical cell, and the first oxygen sensor has a shorter response time than the second oxygen sensor.

For the purposes of the present invention, generative production is understood to mean the construction of a three-dimensional component one layer or level at a time using a powder bed, a powder feed or a wire feed, which serve as the starting material and are melted by the input of energy, for example via a laser beam, and electron beam or a plasma or electric arc. In this context, reference is made to the generative production methods described in the introduction to the description—3D printing or in the case of solidification by chemical activators, melting and solidification (Laser Engineered Net Shaping (LENS), as Direct Metal Deposition (DMD) or as Laser Additive Manufacturing (LAM)), local sintering or melting (Laser Sintering (SLS), Metal-Laser-Sintering (DMLS), Metal-Laser-Sintering (IMLS), Electron Beam Melting (EBM).

During experiments that were conducted preceding the invention, it was found that the oxygen content of the process gas has a decisive influence on the quality of the components. Therefore, control of the oxygen content must be variable depending on the quality requirements to which the component to be manufactured is subject.

The oxygen content of the process gas may be determined for example by using a "lambda probe". A lambda probe compares the oxygen content in the process gas with the known oxygen content of a reference gas. In this, use is made of the capability of certain ceramics to transport oxygen ions electrolytically. If one side of the ceramic is exposed to a reference gas and the other side of the ceramic is exposed to a process gas, a voltage is generated that is a measure of the difference between the partial oxygen pressures of the two gases.

With a known reference gas, this measurement can be used to determine the oxygen content of the process gas.

However, in many ceramics electrolytic conductivity only occurs at elevated temperatures, of 700° C. for example. Therefore, the lambda probe and the process gas are heated correspondingly for the measurement of the oxygen content. At 700° C., the oxygen in the process gas reacts with any hydrogen in the process gas to form water. This means that the oxygen content of the process gas is reduced by the measurement process. The value for the oxygen content determined by the lambda probe is thus lower than the actual oxygen content in the process gas.

For applications with less stringent requirements regarding the quality of the components and the reproducibility of the process, however, the use of a lambda probe is entirely sufficient. On the other hand, if high-quality components are to be produced, such as safety-critical components in the aviation industry, it is imperative that the method be reproducible. In this case, exact determination and control of the oxygen content in the process gas is essential.

Therefore, in order to determine the oxygen content of the process gas more precisely, a second oxygen sensor is used. According to the invention, either the first oxygen sensor or the second oxygen sensor or both oxygen sensors are used to determine the oxygen content of the process gas depending on the quality requirements to which the component is subject.

Advantageously, a lambda probe is used as the first oxygen sensor. A lambda probe is inexpensive and has a short response time. This means that the lambda probe reacts rapidly to changes in the oxygen content. As was noted earlier, however, the disadvantage of the lambda probe is that the oxygen content it measures is not the same as the actual oxygen content. The reason for this is that the lambda probe brings about a reaction between the existing oxygen and other constituents of the process gas during the measuring process that is to say while the oxygen content is being determined. For components with low quality requirements, however, this is tolerable.

The second oxygen sensor used is a measuring or recording instrument that determines the oxygen content of the gas with a method in which the other constituents of the process gas do not affect the value calculated for the oxygen content.

In a preferred embodiment of the invention, a chemical cell, for example a galvanic or amperometric sensor is used.

The sensor used as the second oxygen sensor preferably operates at a temperature below 500° C. below 300° C., below 100° C. or below 40° C. In these temperature ranges, the speed of any reactions between oxygen and other constituents of the process gas is so slow that practically none of the oxygen is converted during the measurement.

The first and second oxygen sensor may be provided directly in the processing chamber or outside the processing chamber. Accordingly, the process gas in which the oxygen content is to be determined may either remain inside the processing chamber or a part of the process gas may be extracted from the processing chamber and directed to the first and/or second oxygen sensor so that its oxygen content can be determined. It is also possible to provide the first oxygen sensor inside the processing chamber and the second oxygen sensor outside the processing chamber. Of course, the reverse configuration is also possible, i.e. in which the second oxygen sensor is located inside the processing chamber and the first oxygen sensor is outside the processing chamber.

In a preferred variant of the invention, a part of the process gas is extracted from the processing chamber and then returned to the processing chamber. Thus a part of the process gases is transported in a circuit. In this case, the determination of the oxygen content may be carried out on the portion of the process gas that has been extracted from the processing chamber. All or some of the portion of the process gas that was extracted from the processing chamber may be returned to the processing chamber or it may be diverted elsewhere depending on the result of the oxygen content analysis.

Most important for the reproducibility of the generative production method and the quality of the components manufactured is the oxygen content at the immediate processing location where the powder is melted. It is therefore advantageous if the process gas is extracted at a point in the immediate vicinity of the processing location and fed to the first and/or second oxygen sensor. For this purpose, an extraction unit for process gas may be provided for example level with the processing plane on which the most recently deposited powder is located.

If a circulatory flow is provided for the process gas, either out of the processing chamber and back into the processing chamber, or also a closed-loop circulation inside the processing chamber, it is advantageous to draw the portion of the process gas intended for oxygen determination from this circulating stream. This ensures that the oxygen content is determined for the portion of the process gas which also flows past the processing location.

Further parameters of the process gas in the processing chamber or of the stream of process gas that has been extracted from the processing chamber may also be determined and optionally compared with a target value. For example, it is possible to calculate the water vapour content or the dewpoint of the process gas that has been extracted from the processing chamber or the water vapour content or the dewpoint of the gas atmosphere in the processing chamber and compare these values with a predefined reference value. Depending on the result of the comparison of the calculated value with the reference value, all, some or none of the process gas previously extracted from the processing chamber is returned to the processing chamber. Also depending on this result, a portion of the extracted stream may be replaced by inert gas, which is introduced into the processing chamber.

The gas stream that is returned via a circulating line or freshly added process gas is introduced into the processing chamber via one or more inlets, wherein the inlets are preferably arranged in a lower area of the processing chamber. This serves to keep the process parameters stable, and homogeneous metallurgical effects can be achieved during production. In particular, it may be provided that at least some of the process gas is passed through the starting material which is present in the form of a powder bed. Due to the immediate proximity of the area in which the process gas enters the processing chamber to the powder bed and the processing location, a constant atmosphere is generated on the top layer of the component during the generative production of said component.

The method according to the invention may preferably relate to a laser melting method. The starting material is then melted locally by means of a laser beam.

The process gas provided is preferably an inert gas which has a greater density than air at the same temperature, e.g., argon. The inert gas may preferably be at a lower temperature than the temperature of the air which is initially present in the processing chamber. In both cases, the process gas collects in the lower area of the processing chamber where the processing also takes place. The heavier, gas-phase argon forces the lighter air, for example, into the upper region of the processing chamber, where e.g. an outlet is provided to allow the air to escape.

It is also possible to add reactive constituents, in particular reactive gases such as CO or $CO_2$, gases with good thermal conductivity such as He to the process gas.

The process gas may be swirled in the processing chamber by means of at least one fan device. In this way, a homogeneous gas composition through the entire volume of the processing chamber is provided. The sample taken is thus a good representation of the composition of the process gas in the processing chamber.

The oxygen content of the process gas is determined in the manner according to the invention depending on the required quality of the component. In one embodiment of the invention, gas containing no oxygen is added to the process gas and/or the processing chamber, if the measured oxygen content is greater than a predefined comparison value. In this way, the oxygen content of the process gas in the processing chamber can be kept below a predefined maximum value.

The invention enables the rapid production of components which are subject to less stringent quality requirements and/or for which exact reproducibility is not paramount importance. In these cases, the oxygen content of the process gas is determined by means of the first oxygen sensor. The first oxygen sensor is typically of simpler construction and less expensive than the second oxygen sensor. In particular, it is advantageous if the first oxygen sensor has a faster response time than the second oxygen sensor.

On the other hand, the invention also allows the reproducible production of high-quality components. In this case the oxygen content of the process gas is determined by means of the second oxygen sensor. The measurement by the second oxygen sensor is unaffected by the other constituents of the process gas. The oxygen content that was present in the process gas even before the start of the measurement is measured exactly. The measurement has no effect on the oxygen content. This enables the oxygen content to be adjusted precisely and reproducibly. The properties of components produced in this way can be reproduced exactly.

The method according to the invention has proven effective for example in the production of components made of AlSiMg, e.g., AlSi7Mg or AlSi10Mg. The negative effect of oxygen on the quality of the components produced by working titanium powder or titanium-containing powders may also be suppressed.

BRIEF DESCRIPTION OF THE DRAWINGS

The invention and further details of the invention will be explained in greater detail in the following text with reference to embodiments thereof represented schematically in the drawings. In the drawings.

DETAILED DESCRIPTION OF THE INVENTION

Figure 1:
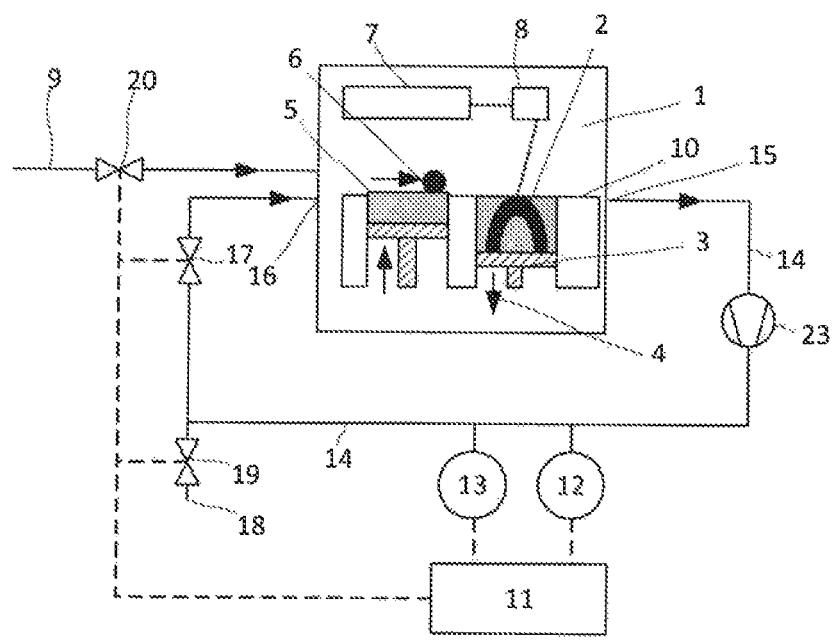
FIG. 1 shows a first apparatus according to the invention for the generative production of a 3-dimensional component and FIG. 2 shows an alternative embodiment of the invention.

FIG. 1 is a schematic representation of an apparatus for carrying out the method according to the invention.

In the following text, an apparatus for generative production of a three-dimensional component is described. As noted earlier, however, the method according to the invention is not limited to the apparatus represented for generative production of three-dimensional components.

The apparatus is a laser melting apparatus. The laser melting apparatus comprises a processing chamber 1 which serves as the construction space for the three-dimensional component 2.

A structuring platform 3 for supporting the component 2 to be produced is arranged inside processing chamber 1. Structuring platform 3 is equipped with a height adjustment device 4, by means of which the height of structuring platform 3 may be adjusted vertically.

Apparatus 1 further comprises a reservoir 5. Reservoir 5 is designed to hold a powder starting material which can be solidified.

Additionally, an application device 6 is provided for depositing the starting material on structuring platform 3. Such an application device 6 is movable horizontally, parallel to work level 10.

A laser 7 for generating a laser beam is also provided. A laser beam generated by laser 7 is deflected via a deflection mechanism 8 and focused on a predetermined point below or in work level 10 through a focusing device (not shown). The path of the laser beam may be altered by deflecting mechanism 8 in such manner that it melts the locations of the deposited layer that correspond to the cross section of the object 2 that is to be produced.

A process gas feed device 9 is also provided, by means of which processing chamber 1 may be charged with a process gas.

Process gas feed device 9 is equipped with one or more reservoirs for the process gas or individual constituents of the process gas, wherein the process gas reservoir (not shown) is connected via one or more line segments to outlets (not shown) which open into the processing chamber. The inlets, e.g., one or more nozzles for introducing process gas are arranged in an lower region of processing chamber 1. The quantity of gas that is introduced is adjustable by means of a control valve 20.

At least one nozzle of the process gas feed device is preferably arranged in the bottom region of processing chamber 1 at a height equivalent to one fifth, one quarter, one half, two thirds or three quarters of the height between the bottom of processing chamber 1 and work level 10 or approximately level with work level 10.

An inert gas such as argon having greater density than air at the same temperature is preferably provided as the process gas.

A fan device (not shown) is also arranged in a bottom region of the processing chamber. Multiple fan devices may also be provided.

A circulating line 14 for a portion of the process gas is also provided. A portion of the process gas may be extracted from processing chamber 1 through an outlet 15, forwarded through circulating line 14 and returned to processing chamber 1 again through inlet 16. The circulation of the process gas is effected for example by means of a blower or compressor 23. A control valve 17 is also provided inside circulating line 14, by means of which the quantity of gas that is returned to processing chamber 1 is controllable. A line 18 is also provided which branches off from circulating line 14 and which makes it possible to draw off the process gas which is transported through circulating line 14. Line 18 is also fitted with a control valve 19.

The apparatus further comprises a controller 11 for controlling control valve 20 of process gas feed device 9 and control valves 17 and 19. Controller 11 may comprise one or preferably two regulating devices (not shown) with a closed control circuit. The regulating devices may also comprise a P-regulator, an I-regulator, a D-regulator and combinations thereof, such as a PID-regulator.

A second oxygen sensor 12 for determining the oxygen content of the process gas circulating through circulating line 14 and a lambda probe 13 for determining the oxygen content of the process gas circulating through circulating line 14 are also provided. The second oxygen sensor 12 and lambda probe 13 are connected to controller 11.

The following text describes a method according to the invention with reference to an embodiment thereof.

Argon is fed into a bottom region of processing chamber 1 as the process gas. Since process gas feed device 9 introduces the process gas at the height of work level 10 or lower, processing chamber 1 is filled with the process gas from the bottom up.

Consequently, the heavier gaseous argon forces the lighter air into the top region of processing chamber 1, in which an outlet (not shown) is provided to allow the air to escape.

The process gas in processing chamber 1 may optionally be agitated by means of a fan device inside processing chamber 1. The turbulence has the effect of removing impurities from dead spaces in the processing chamber. It also creates a homogeneous gas composition throughout the entire volume of the processing chamber. Clean process gas may also be introduced into processing chamber 1 via process gas feed device 9.

A metal starting material is deposited or provided on structuring platform 3 in the form of a powder bed by application device 6. Alternatively, the metallic starting material may also be introduced via a power feed or a wire feed.

Then, the starting material is melted by means of laser 7. The two steps "providing a metal starting material on structuring platform" and "melting the starting material" are repeated multiple times so that the component is constructed layer by layer.

However, the oxygen content of the process gas should not exceed a predetermined maximum value through the manufacturing process in order to avoid undesirable oxidation reactions. According to the invention, the oxygen content of the process gas must therefore be monitored. For this, a sample of the process gas circulating through circulating line 14 is passed to lambda probe 13, and the oxygen content of the sample is determined by lambda probe 13. The oxygen content value obtained thereby is transmitted to controller 11.

In the lambda probe 13, the sample is heated, in which case it is possible for hydrogen and oxygen to recombine to form water. The value calculated by lambda probe 13 for the oxygen content in the sample is therefore not exactly equal to the actual oxygen content of the process gas. For many applications, in which exact reproducibility is not of paramount importance, this inaccuracy is acceptable.

However, if components are to be manufactured with reproducible properties, such as safety-critical components or components which must possess specific minimum mechanical properties for example, even minor variations in the oxygen content are not permissible.

For this reason, in addition to or alternatively to the measurement by the first oxygen sensor, the oxygen content in the process gas or in the process gas that is transported in the circuit may also be determined by means of the second oxygen sensor. For this purpose, a second sample is taken from the process gas and the oxygen content thereof is determined by means of the second oxygen sensor 12. A measuring apparatus or measuring element that functions without any interaction with the other constituents of the process gas is used as the second oxygen sensor 12. In particular, the value measured for the oxygen content is not distorted by the measurement itself.

The value for the hydrogen content calculated by measuring sensor 12 is also transmitted to controller 11. The composition of the process gas in processing chamber 1 is then regulated on the basis of the value calculated for the oxygen content. For this purpose, a portion of the original process gas atmosphere may be diverted via line 18 and/or the composition and/or quantity of process gas fed in through process gas feed device 9 may be adjusted.

Figure 2:
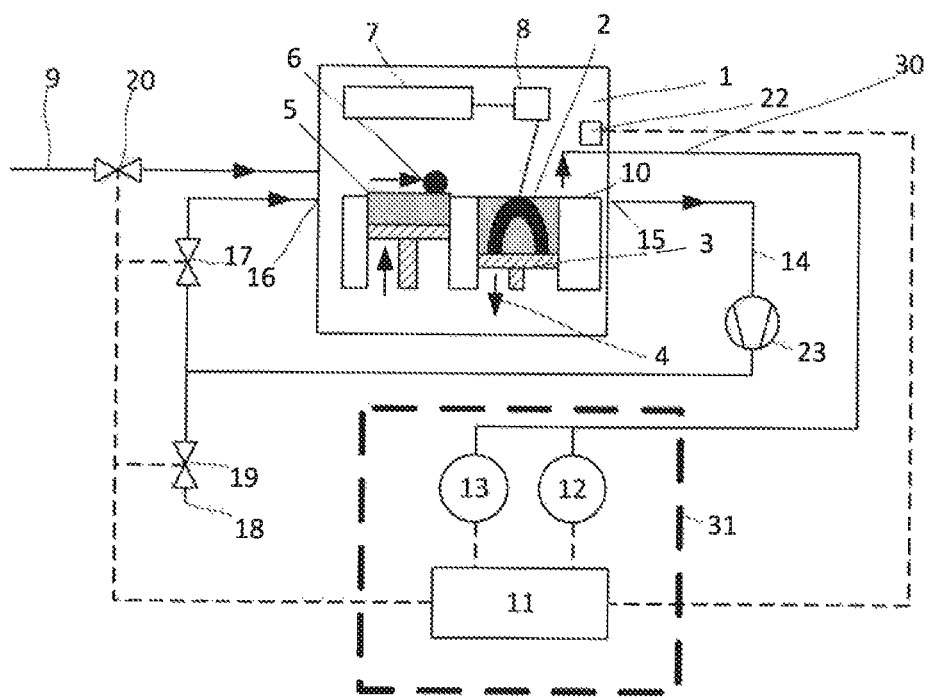

FIG. 2 shows another embodiment of the invention. Identical components are identified with the same reference signs in the two Figures.

The design according to FIG. 2 differs from the one in FIG. 1 essentially in that a separate extraction unit 30 is provided for extracting process gas from processing chamber 1 and transporting it to an analysis device 31. Extraction unit 30 is positioned in the immediate vicinity of the processing location where the powder is melted by laser 7, and within the circulating stream that propels the process gas through processing chamber 1 and circulating line 14. A part of the process gas is forwarded to the first and/or second oxygen sensor 12, 13 via extraction unit 30.

The design according to FIG. 2 also enables existing plants to be upgraded easily for generative production. All that has to be done is to route extraction line 30 into the inside of processing chamber 1. No other direct modifications to the plant are necessary. An external analysis device 31 with first and second oxygen sensors 12, 13 is attached to extraction unit 30 and connected to controller 11 of the existing plant or an external controller. Analysis device 31 switches to oxygen measurement by means of first oxygen sensor 12 or by means of second oxygen sensor 13 depending on the quality standards required.

LIST OF REFERENCE SIGNS

1 Processing chamber
2 Component
3 Structuring platform
4 Height adjustment device
5 Reservoir
6 Application device
7 Laser
8 Deflecting mechanism
9 Process gas feed device
10 Work level
11 Controller
12 Measuring sensor
13 Lambda probe
14 Circulating line
15 Outlet
16 Inlet
17 Control valve
18 Line
19 Control valve
20 Control valve
21 Water vapour measurement
22 Sensor
23 Blower
30 Extraction line
31 Analysis device

What I claim is:

1. A method for the generative production of a three-dimensional component in a processing chamber, comprising:

providing a metal starting material in the processing chamber;
melting the metal starting material by inputting energy from a laser to the metal starting material;
providing a process gas stream in the processing chamber;
extracting a portion of the process gas stream from the processing chamber at a location in the processing chamber of the melting and level with a plane on which a most recently deposited one of the metal starting material is located for at least a portion of the process gas stream flowing through the metal starting material and past where the metal starting material is melted;
generating a constant atmosphere during the generative production on a top layer of the three-dimensional component with the process gas stream;
determining an oxygen content of the portion from the extracting of the process gas stream by providing a first oxygen sensor and a second oxygen sensor, the first oxygen sensor having a faster response time to the oxygen content of the portion of the process gas stream extracted from the location depending on the three-dimensional component to be produced, wherein the oxygen content of the process gas stream determined with the second oxygen sensor is unaffected by and independent of other constituents of the process gas stream and returning the portion extracted of the process gas stream to the processing chamber and diverting another portion of the portion to not return to the processing chamber.

2. The method according to claim 1, wherein the first oxygen sensor comprises a lambda probe.

3. The method according to claim 1, wherein the second oxygen sensor comprises a chemical cell.

4. The method according to claim 1, further comprising feeding a gas without oxygen into the process gas stream if a value for the oxygen content determined with any of the first and second oxygen sensors is greater than a specified comparison value.

5. An apparatus for the generative production of a three-dimensional component, comprising:

a processing chamber with a structuring platform and an application device for depositing starting material on the structuring platform;
a laser for melting the starting material;
a process gas feed device for feeding a process gas stream into the processing chamber;
an extraction unit for extracting a portion of the process gas stream from a location in the processing chamber where the starting material is melted by the laser, the extraction unit provided level with a plane on which a most recently deposited one of the starting material is located such that the portion of the process gas stream flows through the starting material and past the location,
wherein a constant atmosphere is generated during the generative production on a top layer of the three-dimensional component by the process gas stream;
a first oxygen sensor and a second oxygen sensor of different construction than the first oxygen sensor for determining oxygen content of the portion of the process gas stream from the extracting, wherein the second oxygen sensor comprises a chemical cell for the oxygen content unaffected by and independent of other constituents of the process gas stream, and the first oxygen sensor has a faster response time to the oxygen content than the second oxygen sensor and a line for another portion of the portion of the process gas stream to be diverted to not return to the processing chamber.

6. The apparatus according to claim 5, wherein the first oxygen sensor comprises a lambda probe.

7. The apparatus according to claim 5, wherein the second oxygen sensor is operable at a temperature selected from the group consisting of below 500° C., below 300° C., below 100° C., and below 40° C.

8. The apparatus according to claim 5, further comprising a separate analysis device for each of the first and second oxygen sensors.

* * * * *